United States Patent
Kropf et al.

(10) Patent No.: US 11,193,089 B2
(45) Date of Patent: *Dec. 7, 2021

(54) DETERGENTS AND CLEANING AGENTS HAVING ANIONIC SURFACTANTS CONSISTING OF RENEWABLE RAW MATERIALS

(71) Applicant: Henkel AG & Co. KGaA, Duesseldorf (DE)

(72) Inventors: Christian Kropf, Hilden (DE); Alexander Schulz, Essen (DE); Anna Klemmer, Duesseldorf (DE); Regina Palkovits, Aachen (DE); Peter Hausoul, GE Landgraaf (NL); Lukas Kipshagen, Aachen (DE)

(73) Assignee: Henkel AG & Co. KGaA, Duesseldorf (DE)

(*) Notice: Subject to any disclaimer, the term of this patent is extended or adjusted under 35 U.S.C. 154(b) by 164 days.

This patent is subject to a terminal disclaimer.

(21) Appl. No.: 16/272,729

(22) Filed: Feb. 11, 2019

(65) Prior Publication Data
US 2019/0169543 A1 Jun. 6, 2019

Related U.S. Application Data

(63) Continuation of application No. PCT/EP2017/070089, filed on Aug. 8, 2017.

(30) Foreign Application Priority Data

Aug. 12, 2016 (DE) .................... 10 2016 009 800.7

(51) Int. Cl.
*C11D 3/00* (2006.01)
*C11D 3/20* (2006.01)
*C11D 1/26* (2006.01)
*C07D 307/04* (2006.01)

(52) U.S. Cl.
CPC .......... *C11D 3/2096* (2013.01); *C07D 307/04* (2013.01); *C11D 1/26* (2013.01)

(58) Field of Classification Search
CPC .......................... C11D 3/2096; C07D 307/04
See application file for complete search history.

(56) References Cited

U.S. PATENT DOCUMENTS

| 3,855,248 | A | 12/1974 | Lannert et al. |
| 3,923,679 | A | 12/1975 | Rapko |
| 4,013,579 | A | 3/1977 | Nakasone et al. |
| 2017/0369816 | A1* | 12/2017 | Holland ................... C11D 1/75 |

FOREIGN PATENT DOCUMENTS

| GB | 1320178 A | 6/1973 |
| WO | 2015094970 A1 | 6/2015 |

OTHER PUBLICATIONS

PCT International Search Report PCT/EP2017/070089 Completed: Nov. 2, 2017; dated Nov. 10, 2017 2 pages.

* cited by examiner

*Primary Examiner* — Necholus Ogden, Jr.
(74) *Attorney, Agent, or Firm* — Thomas G. Krivulka

(57) ABSTRACT

Detergents and cleaning agents containing an anionic surfactant of general formula (I), in which n is a number from 5 to 21 and $X^+$ is a charge-balancing cation. Also disclosed are an agent or a use, characterized in that, in the compound of general formula (I), $X^+$ is selected from the group including the proton, alkali metal cations and the group $N^+R^1R^2R^3$, where $R^1$, $R^2$ and $R^3$ are, independently of one another, hydrogen, an alkyl group with 1 to 6 C atoms or a hydroxyalkyl group with 2 to 6 C atoms.

9 Claims, No Drawings

DETERGENTS AND CLEANING AGENTS HAVING ANIONIC SURFACTANTS CONSISTING OF RENEWABLE RAW MATERIALS

FIELD OF THE INVENTION

The invention relates to washing or cleaning agents containing anionic surfactants which can be prepared on the basis of renewable raw materials, have low critical micelle concentrations (CMC) and generate low interfacial tensions.

BACKGROUND OF THE INVENTION

It has long been generally known in the field of washing and cleaning agents to use surfactants for reducing the surface tension of water, for forming dispersions and for solubilization. Although several surfactants are prepared, in part or entirely, on the basis of renewable raw materials, some powerful and widely used representatives are still based on petrochemicals. Furthermore, there is a constant desire to provide surfactants that have excellent properties in terms of application in order for it to be possible to achieve high performance even when a low amount of surfactant is used.

BRIEF SUMMARY OF THE INVENTION

A first subject of the invention is a washing or cleaning agent containing a surfactant of general formula (I),

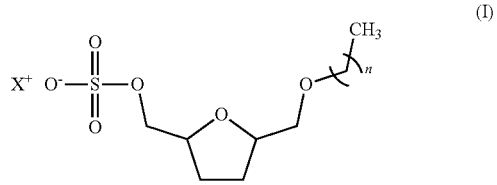

in which n represents a number from 5 to 21, preferably a number from 7 to 17, and $X^+$ represents a charge-balancing cation. $X^+$ is preferably selected from the group comprising the proton, alkali metal cations and the group $N^+R^1R^2R^3$, in which $R^1$, $R^2$ and $R^3$ represent, independently of one another, hydrogen, an alkyl group having 1 to 6 C atoms or a hydroxyalkyl group having 2 to 6 C atoms.

Another subject of the present invention is the use of an anionic surfactant of general formula (I) for increasing the performance of washing or cleaning agents when washing laundry or cleaning hard surfaces.

An agent according to the invention preferably contains from 1 wt. % to 99 wt. %, in particular from 3 wt. % to 85 wt. %, and particularly preferably from 5 wt. % to 65 wt. %, of the surfactant of general formula (I).

Surfactants of general formula (I) can be prepared by sulfating a compound of general formula (II),

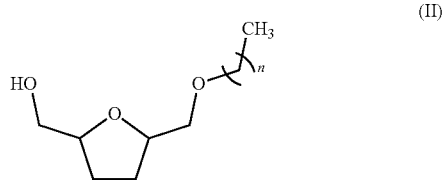

in which n has the meaning indicated above, using a sulfating agent, for example chlorosulfonic acid, and by optional neutralization by subsequent reaction with $X^+OH^-$, where $X^+$ has the meaning indicated above. Compounds of general formula (II) can be obtained by monoalkylation of 2,5-bis(hydroxymethyl)-tetrahydrofuran with primary alkyl halides or alkyl trifluoromethanesulfonates. 2,5-bis(hydroxymethyl)-tetrahydrofuran can be obtained by hydrogenation of hydroxymethylfurfural, an intermediate from the conversion of cellulose. In particular, if alkyl chain mixtures are used in the preparation of the surfactants, n can also assume non-integer values as variables to be determined analytically. Since hydrogenation generally has a low degree of stereoselectivity and since alkylation is generally not stereoselective, the surfactants of general formula (I) are normally present as diastereomer mixtures. Surfactants of general formula (I) and methods for the preparation thereof are described in the international patent application WO 2015/094970 A1.

The surfactants of general formula (I) can be obtained, as described, from renewable raw materials. They are also advantageous in that the renewable raw materials from which they can be prepared do not form a basis for obtaining food, and therefore the food competition situation that is observed in some surfactants that can be obtained from other renewable raw materials does not exist in this case.

The surfactants of general formula (I) are therefore extremely suitable as ingredients in washing and cleaning agents, cosmetic products, such as shampoo and toothpaste, and for the other fields of use in which anionic surfactants have before now usually been used, such as in the food industry, geoscience, tertiary oil production, plastics technology, metalworking, photography, paper recycling, tool cleaning and firefighting.

In addition to the anionic surfactant of general formula (I), a washing or cleaning agent may contain further ingredients which further improve the practical and/or aesthetic properties of the agent. Within the scope of the present invention, the agent preferably additionally contains one or more substances from the group of non-ionic surfactants, anionic surfactants, builders, bleaching agents, bleach activators, enzymes, electrolytes, pH adjusters, perfumes, perfume carriers, fluorescing agents, dyes, hydrotropic substances, foam inhibitors, anti-redeposition agents, graying inhibitors, anti-shrink agents, anti-crease agents, dye transfer inhibitors, antimicrobial active ingredients, non-aqueous solvents, germicides, fungicides, antioxidants, preservatives, corrosion inhibitors, antistatic agents, bittering agents, ironing aids, repellents and impregnating agents, skincare active ingredients, anti-swelling and anti-slip agents, softening components and UV absorbers.

DETAILED DESCRIPTION OF THE INVENTION

An agent according to the invention preferably contains, in addition to the anionic surfactant of general formula (I), up to 99 wt. %, in particular from 3 wt. % to 85 wt. %, and particularly preferably from 5 wt. % to 65 wt. %, of a further surfactant, the additionally present surfactants preferably also being obtainable from renewable raw materials.

An agent according to the invention may contain non-ionic surfactants. Suitable non-ionic surfactants include alkoxylated fatty alcohols, alkoxylated fatty acid alkyl esters, fatty acid amides, alkoxylated fatty acid amides, polyhydroxy fatty acid amides, alkylphenol polyglycol ethers, amine oxides, alkyl polyglucosides and mixtures thereof.

Ethoxylated, in particular primary, alcohols preferably having 8 to 18 C atoms and, on average, 4 to 12 mol of ethylene oxide (EO) per mol of alcohol, in which the alcohol functional group is linear, are preferably used as alkoxylated fatty alcohols. Alcohol ethoxylates having 12 to 18 C atoms, for example of coconut, palm, tallow fatty or oleyl alcohol, and an average of 5 to 8 EO per mol of alcohol are particularly preferred. Examples of preferred ethoxylated alcohols are $C_{12-14}$ alcohols having 4 EO or 7 EO, $C_{9-11}$ alcohol having 7 EO, $C_{12-18}$ alcohols having 5 EO or 7 EO, and mixtures thereof. The degrees of ethoxylation indicated represent statistical averages that can correspond to an integer or a fractional number for a specific product. Preferred alcohol ethoxylates have a narrowed homolog distribution (narrow range ethoxylates, NRE). In addition to these non-ionic surfactants, fatty alcohols having more than 12 EO can also be used. Examples of these are tallow fatty alcohols having 14 EO, 25 EO, 30 EO, or 40 EO. Non-ionic surfactants that contain EO and PO groups together in the molecule can also be used according to the invention. Furthermore, a mixture of a (more highly) branched ethoxylated fatty alcohol and an unbranched ethoxylated fatty alcohol is also suitable, such as a mixture of a $C_{16-18}$ fatty alcohol having 7 EO and 2-propylheptanol having 7 EO. The amount of the non-ionic surfactant is preferably up to 25 wt. %, in particular from 1 wt. % to 20 wt. %, the amount in wt. % referring here and in the following to the total washing agent, unless specified otherwise.

Anionic surfactants that are optionally additionally present include alkyl benzene sulfonic acid salts, olefin sulfonic acid salts, $C_{12-18}$ alkane sulfonic acid salts, salts of sulfuric acid monoesters with a fatty alcohol, a fatty acid soap, salts of sulfuric acid monoesters with an ethoxylated fatty alcohol, or a mixture of two or more of these anionic surfactants.

Surfactants of the sulfonate type that can be used for example are $C_{9-13}$ alkylbenzene sulfonates, olefin sulfonates, i.e. mixtures of alkene and hydroxyalkane sulfonates, and disulfonates, as obtained, for example, from $C_{12-18}$ monoolefins having a terminal or internal double bond by way of sulfonation with gaseous sulfur trioxide and subsequent alkaline or acid hydrolysis of the sulfonation products. $C_{12-18}$ alkane sulfonates and the esters of α-sulfo-fatty acids (ester sulfonates) are also suitable, for example the α-sulfonated methyl esters of hydrogenated coconut, palm kernel or tallow fatty acids.

The salts of the sulfuric acid half esters of $C_{12}$-$C_{18}$ fatty alcohols, for example from coconut fatty alcohol, tallow fatty alcohol, lauryl alcohol, myristyl alcohol, cetyl alcohol or stearyl alcohol, or of $C_{10}$-$C_{20}$ oxo alcohols and the half esters of secondary alcohols having this chain length, are preferred as alk(en)yl sulfates. From a washing perspective, the $C_{12}$-$C_{16}$ alkyl sulfates, $C_{12}$-$C_{15}$ alkyl sulfates and $C_{14}$-$C_{15}$ alkyl sulfates are preferred.

Fatty alcohol ether sulfates, such as the sulfuric acid monoesters of straight-chain or branched $C_{7-21}$ alcohols ethoxylated with 1 to 6 mol of ethylene oxide, such as 2-methyl-branched $C_{9-11}$ alcohols having, on average, 3.5 mol of ethylene oxide (EO) or $C_{12-18}$ fatty alcohols having 1 to 4 EO, are also suitable.

Other suitable anionic surfactants are fatty acid soaps. Saturated and unsaturated fatty acid soaps are suitable, such as the salts of lauric acid, myristic acid, palmitic acid, stearic acid, (hydrogenated) erucic acid and behenic acid, and in particular soap mixtures derived from natural fatty acids, such as coconut, palm kernel, olive oil or tallow fatty acids.

The additional anionic surfactants, including the fatty acid soaps, can be present in the form of the sodium, potassium, magnesium or ammonium salts thereof. The anionic surfactants are preferably present in the form of the sodium or ammonium salts thereof. Amines that can be used for neutralization are preferably choline, triethylamine, monoethanolamine, diethanolamine, triethanolamine, methylethylamine, or a mixture thereof, monoethanolamine being preferred. In a particularly preferred embodiment, the agent contains, in particular when it is present in liquid form, alkyl benzene sulfonic acid, in particular $C_{9-13}$ alkyl benzene sulfonic acid, neutralized with monoethanolamine, and/or fatty acid neutralized with monoethanolamine.

The content of the additional anionic surfactant, if present, in the agent according to the invention is preferably up to 30 wt. %, in particular from 1 wt. % to 25 wt. %.

An agent according to the invention preferably contains at least one water-soluble and/or water-insoluble, organic and/or inorganic builder. The water-soluble organic builders include polycarboxylic acids, in particular citric acid and saccharic acids, monomeric and polymeric aminopolycarboxylic acids, in particular glycinediacetic acid, methylglycinediacetic acid, nitrilotriacetic acid, iminodisuccinates, such as ethylenediamine-N,N'-disuccinic acid and hydroxy iminodisuccinates, ethylenediaminetetraacetic acid and polyaspartic acid, polyphosphonic acids, in particular amino tris(methylenephosphonic acid), ethylenediamine tetrakis (methylenephosphonic acid), lysintetra(methylenephosphonic acid) and 1-hydroxyethane-1,1-diphosphonic acid, polymeric hydroxy compounds such as dextrin, and polymeric (poly)carboxylic acids, in particular polycarboxylates that can be obtained by oxidation of polysaccharides, polymeric acrylic acids, methacrylic acids, maleic acids, and mixed polymers thereof, which may also contain small portions of polymerizable substances, without a carboxylic acid functionality, in the polymer. The average relative molecular mass of the homopolymers of unsaturated carboxylic acids is generally between 5,000 g/mol and 200,000 g/mol, and the average relative molecular mass of the copolymers is between 2,000 g/mol and 200,000 g/mol, preferably between 50,000 g/mol and 120,000 g/mol, based in each case on the free acid. A particularly preferred acrylic acid-maleic acid copolymer has an average relative molecular mass of from 50,000 to 100,000. Compounds of this class which are suitable, although less preferred, are copolymers of acrylic acid or methacrylic acid with vinyl ethers, such as vinyl methyl ethers, vinyl esters, ethylene, propylene, and styrene, in which the proportion of the acid is at least 50 wt. %. Terpolymers which contain, as monomers, two unsaturated acids and/or the salts thereof and, as the third monomer, vinyl alcohol and/or a vinyl alcohol derivative or a carbohydrate can also be used as water-soluble organic builders. The first acidic monomer or the salt thereof is derived from a monoethylenic unsaturated $C_3$-$C_8$ carboxylic acid and preferably from a $C_3$-$C_4$ monocarboxylic acid, in particular from (meth)acrylic acid. The second acidic monomer or the salt thereof can be a derivative of a $C_4$-$C_8$ dicarboxylic acid, maleic acid being particularly preferred. The third monomeric unit is formed in this case of vinyl alcohol and/or preferably an esterified vinyl alcohol. In particular, vinyl alcohol derivatives are preferred, which constitute an ester of short-chain carboxylic acids, for example of $C_1$-$C_4$ carboxylic acids, with vinyl alcohol. Preferred polymers contain from 60 wt. % to 95 wt. %, in particular from 70 wt. % to 90 wt. %, of (meth)acrylic acid or (meth)acrylate, particularly preferably acrylic acid or acrylate, and maleic acid or maleinate, and from 5 wt. % to 40 wt. %, preferably from 10 wt. % to 30 wt. %, of vinyl alcohol and/or vinyl acetate. Very particularly preferred are polymers in which the weight ratio of (meth)acrylic acid or (meth)acrylate to maleic acid or maleinate is between 1:1 and 4:1, preferably between 2:1 and 3:1 and in particular between 2:1 and 2.5:1. The amounts and the weight ratios refer to the acids in this case. The second acidic monomer or the salt thereof may also be a derivative of an allyl sulfonic acid which is substituted in position 2 with an alkyl functional group, preferably with a $C_1$-$C_4$ alkyl functional group, or an aromatic functional group which is preferably derived from benzene or benzene derivatives. Preferred terpolymers contain from 40 wt. % to 60 wt. %, in particular from 45 to 55 wt. %, of (meth)acrylic acid or (meth)acrylate, particularly preferably acrylic acid or acrylate, from 10 wt. % to 30 wt. %, preferably from 15 wt. % to 25 wt. %, of methallyl sulfonic acid or methallyl sulfonate and, as the third monomer, from 15 wt. % to 40 wt. %, preferably from 20 wt. % to 40 wt. %, of a carbohydrate. This carbohydrate may be, for example, a monosaccharide, disaccharide, oligosaccharide or polysaccharide, with monosaccharides, disaccharides or oligosaccharides being preferred. Saccharose is particularly preferred. By inserting the third monomer, break points are presumably incorporated into the polymer which are responsible for the high biodegradability of the polymer. These terpolymers generally have an average relative molecular mass of between 1,000 g/mol and 200,000 g/mol, preferably between 200 g/mol and 50,000 g/mol. Further preferred copolymers are those which comprise acrolein and acrylic acid/acrylic acid salts or vinyl acetate as monomers. The organic builders may, in particular for the preparation of liquid agents, be used in the form of aqueous solutions, preferably in the form of 30 to 50 wt. % aqueous solutions. All indicated acids are generally used in the form of the water-soluble salts thereof, in particular alkali salts thereof.

Organic builders of this kind may, if desired, be contained in amounts of up to 40 wt. %, in particular up to 25 wt. %, and preferably from 1 wt. % to 8 wt. %.

Amounts in the upper half of the stated ranges are preferably used in paste-form or liquid, in particular water-containing, agents.

In particular polyphosphates, preferably sodium triphosphate, are suitable as water-soluble inorganic builder materials. In particular crystalline or amorphous water-dispersible alkali aluminosilicates are used as water-insoluble inorganic builder materials in amounts of no greater than 25 wt. %, preferably from 3 wt. % to 20 wt. %, and in particular in amounts from 5 wt. % to 15 wt. %. Among these, crystalline sodium aluminosilicates of washing agent quality, in particular zeolite A, zeolite P, zeolite MAP and optionally zeolite X, are preferred. Amounts close to the stated upper limit are preferably used in solid particulate agents. Suitable aluminosilicates have, in particular, no particles having a particle size greater than 30 μm and preferably comprise at least 80 wt. % of particles having a size smaller than 10 μm. The calcium binding capacity thereof is generally in the range of from 100 to 200 mg CaO per gram.

In addition, or as an alternative to the mentioned water-insoluble aluminosilicate and alkali carbonate, further water-soluble inorganic builder materials may be contained. These include, in addition to polyphosphates such as sodium triphosphate, in particular water-soluble crystalline and/or amorphous alkali silicate builders. Water-soluble inorganic builder materials of this kind are contained in the agents preferably in amounts of from 1 wt. % to 20 wt. %, in particular from 5 wt. % to 15 wt. %. The alkali silicates that can be used as builder materials preferably have a molar ratio of alkali oxide to $SiO_2$ of less than 0.95, in particular from 1:1.1 to 1:12, and may be present in amorphous or crystalline form. Preferred alkali silicates are sodium silicates, in particular amorphous sodium silicates having a $Na_2O:SiO_2$ molar ratio of from 1:2 to 1:2.8. Preferably used as crystalline silicates, which may be present in isolation or in a mixture with amorphous silicates, are crystalline phyllosilicates of general formula $Na_2Si_xO_{2x+1} \cdot y\ H_2O$, where x, referred to as the module, is a number from 1.9 to 4, y is a number from 0 to 20, and preferred values for x are 2, 3 or 4. Preferred crystalline phyllosilicates are those in which x in the stated general formula assumes the values 2 or 3. Both ß and δ-sodium disilicates ($Na_2Si_2O_5 \cdot y\ H_2O$) are particularly preferred. Practically water-free crystalline alkali silicates which have the above general formula, in which x is a number from 1.9 to 2.1, and which are prepared from amorphous alkali silicates may also be used in the agents. In a further preferred embodiment, a crystalline sodium phyllosilicate having a module of from 2 to 3, as can be prepared from sand and soda, is used. Sodium silicates having a module in the range of from 1.9 to 3.5 are used in a further embodiment. In a preferred embodiment of agents of this kind, a granulate compound consisting of alkali silicate and alkali carbonate is used, such as is commercially available under the name Nabion® 15, for example.

Suitable peroxidic bleaching agents are, in particular, organic peracids or peracid salts of organic acids, such as phthalimidopercaproic acid, perbenzoic acid, monoperoxyphthalic acid, and diperdodecanedioic acid and the salts thereof, such as magnesium monoperoxyphthalate, diacyl peroxides, hydrogen peroxide and inorganic salts which release hydrogen peroxide under the conditions of use, such as alkali perborate, alkali percarbonate and/or alkali persilicate, and hydrogen peroxide inclusion compounds, such as $H_2O_2$ urea adducts, and mixtures thereof. Hydrogen peroxide can also be produced by means of an enzymatic system, i.e. an oxidase and the substrate thereof. If solid peroxygen compounds are intended to be used, these may be used in the form of powders or granules, which may also be coated in a manner known in principle. It is particularly preferable to use alkali percarbonate, alkali perborate monohydrate or hydrogen peroxide. A washing agent which can be used within the scope of the invention contains a peroxidic bleaching agent in amounts of preferably up to 60 wt. %, in particular from 5 wt. % to 50 wt. % and particularly preferably from 15 wt. % to 30 wt. % or, alternatively, from 2.5 wt. % to 20 wt. %, hydrogen peroxide being the particularly preferred peroxidic bleaching agent in liquid agents and sodium percarbonate being the particularly preferred peroxidic bleaching agent in solid agents. Peroxidic bleaching agent particles preferably have a particle size in the range of from 10 μm to 5,000 μm, in particular from 50 μm to 1,000 μm, and/or have a density of from 0.85 g/cm$^3$ to 4.9 g/cm$^3$, in particular from 0.91 g/cm$^3$ to 2.7 g/cm$^3$.

Compounds that, under perhydrolysis conditions, result in optionally substituted perbenzoic acid and/or aliphatic peroxycarboxylic acids having 1 to 12 C atoms, in particular 2 to 4 C atoms, either in isolation or in mixtures, can be used as bleach-activating compounds which yield peroxocarboxylic acid under perhydrolysis conditions. Bleach activators that carry O and/or N acyl groups in particular having the indicated number of C atoms and/or optionally substituted benzoyl groups are suitable. Preferred are polyacylated alkylene diamines, in particular tetraacetylethylenediamine (TAED), acylated glycolurils, in particular tetraacetyl glycoluril (TAGU), acylated triazine derivatives, in particular 1,5-diacetyl-2,4-dioxohexahydro-1,3,5-triazine (DADHT), N-acylimides, in particular N-nonanoyl succinimide (NOSI), acylated phenolsulfonates or carboxylates or the sulfonic or carboxylic acids thereof, in particular n-nonanoyl, isononanoyl or lauroyloxybenzenesulfonate (NOBS, iso-NOBS or LOBS) or decanoyloxybenzoate (DOBA), the formal carboxylic acid ester derivatives thereof, such as 4-(2-decanoyloxyethoxycarbonyloxy)-benzene sulfonate (DECOBS), acylated polyhydric alcohols, in particular triacetin, ethylene glycol diacetate, 2,5-diacetoxy-2,5-dihydrofuran and acetylated sorbitol and mannitol and the mixtures thereof (SORMAN), acylated sugar derivatives, in particular pentaacetyl glucose (PAG), pentaacetyl fructose, tetraacetyl xylose and octaacetyl lactose, acetylated, optionally N-alkylated, glucamine and gluconolactone, and/or N-acylated lactams, for example N-benzoylcaprolactam.

In addition to or in place of the compounds which form peroxycarboxylic acids under perhydrolysis conditions, further bleach-activating compounds, such as nitriles, from which perimidic acids are formed under perhydrolysis conditions, may be present. These include in particular aminoacetonitrile derivatives having a quaternized nitrogen atom according to formula

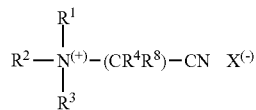

in which $R^1$ represents —H, —$CH_3$, a $C_{2-24}$ alkyl or alkenyl functional group, a substituted $C_{1-24}$ alkyl or $C_{2-24}$ alkenyl functional group having at least one substituent from the group —Cl, —Br, —OH, —$NH_2$, —CN and —$N^{(+)}$—$CH_2$—CN, an alkyl or alkenylaryl functional group having a $C_{1-24}$ alkyl group, or a substituted alkyl or alkenylaryl functional group having at least one, preferably two, optionally substituted $C_{1-24}$ alkyl group(s) and optionally further substituents on the aromatic ring, $R^2$ and $R^3$ are selected, independently of one another, from —$CH_2$—CN, —$CH_3$, —$CH_2$—$CH_3$, $CH_2$—$CH_2$—$CH_3$, —CH($CH_3$)—$CH_3$, —$CH_2$—OH, —$CH_2$—$CH_2$—OH, —CH(OH)—$CH_3$, —$CH_2$—$CH_2$—$CH_2$—OH, —$CH_2$—CH(OH)—$CH_3$, —CH(OH)—$CH_2$—$CH_3$, —($CH_2CH_2$—O)$_n$H where n=1, 2, 3, 4, 5 or 6, $R^4$ and $R^5$ have, independently of one another, a meaning indicated above for $R^1$, $R^2$ or $R^3$, it being possible for at least two of the mentioned functional groups, in particular $R^2$ and $R^3$, to be linked so as to close the ring even when the nitrogen atom and optionally further heteroatoms are included, and said functional groups then preferably forming a morpholino ring, and X is a charge-balancing anion, preferably selected from benzene sulfonate, toluene sulfonate, cumene sulfonate, $C_{9-15}$ alkylbenzene sulfonates, $C_{1-20}$ alkyl sulfates, $C_{8-22}$ carboxylic acid methyl ester sulfonates, sulfate, hydrogen sulfate and the mixtures thereof. Bleach activators which form peroxycarboxylic acids or perimidic acids under perhydrolysis conditions are preferably present in agents according to the invention in amounts of up to 25 wt. %, in particular from 0.1 wt. % to 10 wt. %. Bleach activator particles preferably have a particle size in the range of from 10 µm to 5,000 in particular from 50 µm to 1,000 and/or have a density of from 0.85 g/cm$^3$ to 4.9 g/cm$^3$, in particular from 0.91 g/cm$^3$ to 2.7 g/cm$^3$.

It is possible for bleach-catalyzing transition metal complexes to be present, in addition to or in place of the mentioned bleach activators. These are preferably selected from cobalt, iron, copper, titanium, vanadium, manganese and ruthenium complexes. Ligands in transition metal complexes of this kind are both inorganic and organic compounds, including, in addition to carboxylates, in particular compounds having primary, secondary and/or tertiary amine and/or alcohol functions, such as pyridine, pyridazine, pyrimidine, pyrazine, imidazole, pyrazole, triazole, 2,2'-bispyridylamine, tris-(2-pyridylmethyl)amine, 1,4,7-triazacyclononane, 1,4,7-trimethyl-1,4,7-triazacyclononane, 1,5,9-trimethyl-1,5,9-triazacyclododecane, (bis-((1-methylimidazol-2-yl)-methyl))-(2-pyridylmethyl)-amine, s-(1-methylimidazol-2-yl)-methyl)-ethylendiamine, N-bis-(2-benzimidazolylmethyl)-aminoethanol, 2,6-bis-(bis-(2-benzimidazolylmethyl)aminomethyl)-4-methylphenol, N,N,N',N'-tetrakis-(2-benzimidazolylmethyl)-2-hydroxy-1,3-diaminopropane, 2,6-bis-(bis-(2-pyridylmethyl)aminomethyl)-4-methylphenol, 1,3-bis-(bis-(2-benzimidazolyl-methyl)aminomethyl)-benzene, sorbitol, mannitol, erythritol, adonitol, inositol, lactose, and optionally substituted salens, porphins and porphyrins. The inorganic neutral ligands include in particular ammonia and water. If not all coordination sites of the transition metal central atom are occupied by neutral ligands, the complex contains further, preferably anionic, ligands, and among these in particular monodentate or bidentate ligands. These include in particular the halides, such as fluoride, chloride, bromide and iodide, and the $(NO_2)^-$ group, i.e. a nitro ligand or a nitrito ligand. The $(NO_2)^-$ group may also be chelated to a transition metal or it may asymmetrically bridge or µl-O bridge two transition metal atoms. In addition to the ligands mentioned, the transition metal complexes may carry further, generally simpler, ligands, in particular monovalent or polyvalent anion ligands. These include, for example, nitrate, acetate, trifluoroacetate, formate, carbonate, citrate, oxalate, perchlorate and complex anions such as hexafluorophosphate. The anion ligands are intended to provide charge balance between the transition metal central atom and the ligand system. It is also possible for oxo ligands, peroxo ligands and imino ligands to be present. In particular, ligands of this kind can also have a bridging effect such that polynuclear complexes are formed. In the case of bridged, dinuclear complexes, the two metal atoms in the complex need not be the same. It is also possible to use binuclear complexes in which the two transition metal central atoms have different oxidation numbers. If anionic ligands are not present or if the presence of anionic ligands does not result in charge balancing in the complex, anionic counterions which neutralize the cationic transition metal complex are present in the transition metal complex compounds to be used according to the invention. These anionic counterions include in particular nitrate, hydroxide, hexafluorophosphate, sulfate, chlorate, perchlorate, the halides such as chloride or the anions of carboxylic acids such as formate, acetate, oxalate, benzoate or citrate. Examples of transition metal complex compounds that can be used are [N,N'-bis[(2-hydroxy-5-vinylphenyl)-methylene]-1,2-diamino-cyclohexane]-manganese-(III)-chloride, [N,N'-bis[(2-hydroxy-5-nitrophenyl)-methylene]-1,2-diamino-cyclohexane]-manganese-(III)-acetate, [N,N'-bis[(2-hydroxyphenyl)-methylene]-1,2-phenylendiamine]-manganese-(III)-acetate, [N,N'-bis[(2-hydroxyphenyl)-methylene]-1,2-diaminocyclohexane]-manganese-(III)-chloride, [N,N'-bis[(2-hydroxyphenyl)-methylene]-1,2-diaminoethane]-manganese-(lll)-chloride, [N,N'-bis[(2-hydroxy-5-sulfonatophenyl)-methylene]-1,2-diaminoethane]-manganese-(lll)-chloride, manganese-oxalato complexes, nitropentammine-cobalt (lll)-chloride, nitritopentammine-cobalt(III)-chloride, hexammincobalt(III)-chloride, chloropentammine-cobalt(III)-chloride and the peroxo complex $[(NH_3)_5Co-O-O-Co(NH_3)_5]Cl_4$.

Suitable as enzymes that can be used in the agents are those from the class of proteases, amylases, lipases, cutinases, pullulanases, hemicellulases, cellulases, oxidases, laccases and peroxidases, and the mixtures thereof. Enzymatic active ingredients obtained from fungi or bacteria, such as *Bacillus subtilis, Bacillus licheniformis, Bacillus lentus, Streptomyces griseus, Humicola lanuginosa, Humicola insolens, Pseudomonas pseudoalcaligenes, Pseudomonas cepacia* or *Coprinus cinereus* are particularly suitable. The enzymes may be adsorbed on carrier substances and/or embedded in coating substances to protect the enzymes from premature inactivation. The enzymes are preferably contained in the washing or cleaning agents according to the invention in amounts of up to 5 wt. %, in particular from 0.002 wt. % to 4 wt. %. If the agent according to the invention contains protease, it preferably has a proteolytic activity in the range of from approximately 100 PE/g to approximately 10,000 PE/g, in particular from 300 PE/g to 8,000 PE/g. If a plurality of enzymes are intended to be inserted in the agent according to the invention, this can be carried out by incorporating two or more separate enzymes or two or more enzymes that are separately packaged in a known manner, or by two or more enzymes packaged together in a granulate.

In order to set a desired pH that does not result automatically from mixing the other components, the agents according to the invention may contain acids that are compatible with the system and the environment, in particular citric acid, acetic acid, tartaric acid, malic acid, lactic acid, glycolic acid, succinic acid, glutaric acid, and/or adipic acid, but also mineral acids, in particular sulfuric acid, or bases, in particular ammonium or alkali hydroxides. pH regulators of this kind are contained in the agents according to the invention preferably in amounts of no greater than 20 wt. %, in particular from 1.2 wt. % to 17 wt. %.

The function of graying inhibitors is to keep the dirt that is removed from the textile fiber suspended in the liquor. Water-soluble colloids, which are usually organic, are suitable for this purpose, for example starch, sizing material, gelatin, salts of ethercarboxylic acids or ethersulfonic acids of starch or of cellulose, or salts of acidic sulfuric acid esters of cellulose or of starch. Water-soluble polyamides containing acidic groups are also suitable for this purpose. Starch derivatives other than those mentioned above may also be used, for example aldehyde starches. Cellulose ethers, such as carboxymethylcellulose (Na salt), methylcellulose, hydroxyalkylcellulose, and mixed ethers, such as methylhydroxyethylcellulose, methylhydroxypropylcellulose, methylcarboxymethylcellulose and the mixtures thereof, are preferably used, for example, in amounts of from 0.1 to 5 wt. %, based on the agents.

The agents may, if desired, contain a conventional dye transfer inhibitor, preferably in amounts of up to 2 wt. %, in particular from 0.1 wt. % to 1 wt. %, which, in a preferred embodiment, is selected from polymers of vinylpyrrolidone, vinyl imidazole or vinyl pyridine-N-oxide, or copolymers thereof. Polyvinylpyrrolidones having molar weights of from 15,000 g/mol to 50,000 g/mol and polyvinylpyrrolidones having higher molar weights of, for example, up to 1,000,000 g/mol, in particular from 1,500,000 g/mol to 4,000,000 g/mol, N-vinylimidazole/N-vinylpyrrolidone copolymers, polyvinyloxazolidones, copolymers based on vinyl monomers and carboxylic acid amides, pyrrolidone group-containing polyesters and polyamides, grafted polyamidoamines and polyethyleneimines, polyamine-N-oxide polymers and polyvinyl alcohols may be used. However, enzymatic systems comprising a peroxidase and hydrogen peroxide or a substance which yields hydrogen peroxide in water can also be used. In this case, it is preferable to add a mediator compound for the peroxidase, for example an acetosyringone, a phenol derivative, a phenothiazine or a phenoxazine, it being possible to also use above-mentioned polymeric dye transfer inhibitor active ingredients. Polyvinylpyrrolidone preferably has an average molar mass in the range of from 10,000 g/mol to 60,000 g/mol, in particular in the range of from 25,000 g/mol to 50,000 g/mol. From among the copolymers, those consisting of vinylpyrrolidone and vinylimidazole in a molar ratio of from 5:1 to 1:1 having an average molar mass in the range of from 5,000 g/mol to 50,000 g/mol, in particular from 10,000 g/mol to 20,000 g/mol are preferred. In preferred embodiments of the invention, the washing agents are however free of additional dye transfer inhibitors of this kind.

Washing agents may contain, for example, derivatives of diaminostilbene disulfonic acid or the alkali metal salts thereof as optical brighteners, even though they are preferably free of optical brighteners for use as color-safe washing agents. Suitable, for example, are salts of 4,4'-bis(2-anilino-4-morpholino-1,3,5-triazinyl-6-amino)stilbene-2,2'-disulfonic acid or similarly constructed compounds which carry a diethanolamino group, a methylamino group, an anilino group or a 2-methoxyethylamino group instead of the morpholino group. Furthermore, brighteners of the substituted diphenyl styryl type may also be present, for example the alkali salts of 4,4'-bis(2-sulfostyryl)-diphenyl, 4,4'-bis(4-chloro-3-sulfostyryl)-diphenyl, or 4-(4-chlorostyryl)-4'-(2-sulfostyryl)-diphenyl. Mixtures of the aforementioned optical brighteners may also be used.

Particularly for use in automatic methods, it may be advantageous for conventional foam inhibitors to be added to the agents. Soaps of natural or synthetic origin that have a high proportion of $C_{18}$-$C_{24}$ fatty acids are, for example, suitable as foam inhibitors. Suitable non-surfactant foam inhibitors are, for example, organopolysiloxanes and the mixtures thereof with microfine, optionally silanated, silicic acid and paraffins, waxes, microcrystalline waxes and the mixtures thereof with silanated silicic acid or bis-fatty acid alkylene diamides. Mixtures of various foam inhibitors are also advantageously used, for example those made up of silicones, paraffins or waxes. The foam inhibitors, in particular silicone and/or paraffin-containing foam inhibitors, are preferably bound to a granular carrier substance that is soluble or dispersible in water. Mixtures of paraffins and bistearylethylenediamide are particularly preferred.

In a preferred embodiment, the agent according to the invention is particulate and contains, in addition to the surfactant of general formula (I), builders, in particular in an amount in the range of from 1 wt. % to 60 wt. %.

In a further preferred embodiment, an agent according to the invention is liquid and contains from 1 wt. % to 90 wt. %, in particular from 10 wt. % to 85 wt. %, preferably from 25 wt. % to 75 wt. %, and particularly preferably from 35 wt. % to 65 wt. %, of water, a water-miscible solvent or a mixture of water and a water-miscible solvent. Water-miscible solvents include, for example, monovalent alcohols having 1 to 4 C atoms, in particular methanol, ethanol, isopropanol, and tert-butanol, diols and triols having 2 to 4 C atoms, in particular ethylene glycol, propylene glycol and glycerol, and the mixtures thereof, and the ethers that are derivable from the mentioned compound classes. Water-miscible solvents of this kind are preferably present in the agents according to the invention in amounts of no greater than 30 wt. %, in particular from 2 wt. % to 20 wt. %.

In a further preferred embodiment, the agent according to the invention is provided in a chamber made of water-soluble material such that it is portioned so as to be ready to be dispensed in individual portions, and the agent preferably contains less than 15 wt. %, in particular in the range of from 1 wt. % to 12 wt. %, of water. A portion is an independent dispensing unit having at least one chamber in which material to be dispensed is contained. A chamber is a space delimited by walls (for example by a film) which can also exist without the material to be dispensed (optionally, with a change in its shape). A surface coating or a layer of a surface coating is thus not a wall according to the present invention.

The walls of the chamber are made of a water-soluble material. The water solubility of the material can be determined by means of a square film of said material (film: 22×22 mm with a thickness of 76 μm) fixed in a square frame (edge length on the inside: 20 mm) according to the following measurement protocol. Said framed film is immersed in 800 ml of distilled water kept at 20° C. in a 1 liter beaker having a circular bottom (Schott, Mainz, 1000 ml beaker, low form) such that the surface of the clamped film is arranged at right angles to the bottom of the beaker, the upper edge of the frame is 1 cm below the water surface and the lower edge of the frame is oriented in parallel with the bottom of the beaker such that the lower edge of the frame extends along the radius of the bottom of the beaker and the center of the lower edge of the frame is located above the center of the radius of the bottom of the beaker. The material dissolves when stirred (stirring speed magnetic stirrer 300 rpm, stir stick: 5 cm long) within 600 seconds in such a way that individual solid particles are no longer visible to the naked eye.

The walls of the chambers and thus the water-soluble wrappings of the washing agents according to the invention are preferably formed by a water-soluble film material. Water-soluble packaging of this kind can be made by vertical form fill sealing methods or by thermoforming methods.

The thermoforming method generally involves forming a first layer of a water-soluble film material in order to form depressions for receiving a composition therein, filling the composition into the depressions, covering the composition-filled depressions with a second layer of a water-soluble film material, and sealing the first and second layers together at least around the depressions.

The water-soluble film material is preferably selected from polymers or polymer mixtures. The wrapping may be formed of one or two or more layers of water-soluble film material. The water-soluble film materials of the first layer and the further layers, if present, may be the same or different.

It is preferable for the water-soluble wrapping to contain polyvinyl alcohol or a polyvinyl alcohol copolymer; particularly preferably, it consists of a polyvinyl alcohol or polyvinyl alcohol copolymer.

Water-soluble films for producing the water-soluble wrapping are preferably based on a polyvinyl alcohol or a polyvinyl alcohol copolymer of which the molecular weight is in the range of from 10,000 to 1,000,000 gmol$^{-1}$, preferably from 20,000 to 500,000 gmol$^{-1}$, particularly preferably from 30,000 to 100,000 gmol$^{-1}$, and in particular from 40,000 to 80,000 gmol$^{-1}$.

Polyvinyl alcohol is usually prepared by hydrolysis of polyvinyl acetate, since the direct synthesis route is not possible. The same applies to polyvinyl alcohol copolymers, which are correspondingly prepared from polyvinyl acetate copolymers. It is preferable for at least one layer of the water-soluble wrapping to comprise a polyvinyl alcohol of which the degree of hydrolysis is from 70 to 100 mol. %, preferably from 80 to 90 mol. %, particularly preferably from 81 to 89 mol. %, and in particular from 82 to 88 mol. %.

Polymers selected from the group comprising acrylic acid-containing polymers, polyacrylamides, oxazoline polymers, polystyrene sulfonates, polyurethanes, polyesters, polyethers, polylactic acid, and/or mixtures of the above polymers may additionally be added to a film material suitable for producing the water-soluble wrapping. The copolymerization of monomers forming the basis of polymers of this kind, individually or in mixtures of two or more, with vinyl acetate is also possible.

Preferred polyvinyl alcohol copolymers include, in addition to vinyl alcohol, an ethylenically unsaturated carboxylic acid, the salts thereof or the esters thereof. Polyvinyl alcohol copolymers of this kind particularly preferably contain, in addition to vinyl alcohol, acrylic acid, methacrylic acid, acrylic acid esters, methacrylic acid esters or mixtures thereof; among the esters, $C_{1-4}$ alkyl esters or hydroxyalkyl esters are preferred. Likewise, preferred polyvinyl alcohol copolymers include, in addition to vinyl alcohol, ethylenically unsaturated dicarboxylic acids, as further monomers. Examples of suitable dicarboxylic acids are itaconic acid, maleic acid, fumaric acid and mixtures thereof, itaconic acid being particularly preferred.

Suitable water-soluble films for use in the wrappings of the water-soluble packaging according to the invention are films marketed by the company MonoSol LLC, for example under the name M8630, C8400 or M8900. Other suitable films include films named Solublon® PT, Solublon® GA, Solublon® KC or Solublon® KL from Aicello Chemical Europe GmbH or the films VF-HP from Kuraray.

The washing or cleaning agent portion comprising the washing or cleaning agent and the water-soluble wrapping may have one or more chambers. The water-soluble wrappings comprising one chamber can have a substantially dimensionally stable spherical, rotationally ellipsoidal, cubic, cuboid or pillow-shaped design having a circular, elliptical, square or rectangular basic shape. The agent may be contained in one or more chambers, if present, of the water-soluble wrapping.

In a preferred embodiment, the water-soluble wrapping has two chambers. In this embodiment, the two chambers may each contain a solid sub-composition or a liquid sub-composition, or the first chamber contains a liquid sub-composition and the second chamber contains a solid sub-composition.

The portions of the agents contained in the different chambers of a water-soluble wrapping having two or more chambers may have the same composition. However, the agents in a water-soluble wrapping having at least two chambers preferably have sub-compositions which differ at least in one ingredient and/or in the content of at least one ingredient. Preferably, a sub-composition of agents of this kind according to the invention comprises an enzyme and/or bleach activator, and a further sub-composition separate therefrom comprises a peroxidic bleaching agent, the sub-composition mentioned first not comprising in particular a peroxidic bleaching agent and the sub-composition mentioned second not comprising in particular an enzyme or bleach activator.

As a result of portion-wise packaging in a water-soluble wrapping, the user is able to supply, for one application, one or, if desired, several, preferably one, of the portions to the washing machine or dishwasher, in particular the dispensing compartment of a washing machine, or a container for carrying out a manual washing or cleaning process. Portion packaging of this kind meets the consumer's desire for simplified dispensing. After water is added, the wrapping material dissolves such that the ingredients are released and can take effect in the liquor. A portion wrapped in water-soluble wrapping preferably weighs from 10 g to 35 g, in particular from 12 g to 28 g, and particularly preferably from 12 g to 15 g, the proportion of the water-soluble wrapping representing from 0.3 g to 2.5 g, in particular from 0.7 g to 1.2 g, based on the weight indicated.

There is no difficulty in preparing solid agents according to the invention, and said agents can be prepared in a known manner, for example by spray drying or granulation, an enzyme and possible further thermally sensitive ingredients, such as bleaching agents, being optionally added separately at a later stage. For the preparation of agents having an increased bulk weight, in particular in the range of from 650 g/l to 950 g/l, a method having an extrusion step is preferred.

Liquid or pasty agents according to the invention in the form of solutions containing water conventional solvents are generally prepared by simply mixing the ingredients, which can be added in bulk or as a solution in an automatic mixer.

EXAMPLES

Similarly to the method disclosed in Example 7 of WO 2015/094970, sodium 5-((dodecyloxy)methyl)tetrahydrofuran-2-yl)methyl sulfate (P1) was prepared from 5-((dodecyloxy)methyl)tetrahydrofuran-2-yl)methanol obtained according to Example 5 of said patent application. Its critical micelle concentration (CMC) was determined by measuring the surface tension of an aqueous solution of P1 as a function of the concentration at 25° C. and a pH of from 8.5 to 0.02 g/l. The interfacial tension of an aqueous solution of P1 (concentration 1 g/l) with respect to isopropyl myristate at pH 8.5 and 25° C. was measured using the spinning drop method. After 20 minutes, the value was 4 mN/m.

The washing performance of P1 was tested in washing tests in miniaturized form on the standardized cotton stains set forth in Table 1, unless specified otherwise. At a washing temperature of 40° C., a washing time of 1 h and a dosage of 4.1 g/l of a washing agent V1, which was free of surfactants according to general formula (I), or a dosage of 4.1 g/l of a washing agent M1, the composition of which was the same as V1, except 2 wt. % of the surfactant P1 was additionally contained, the differences in the brightness values after and before washing (ΔΔY values) also shown in Table 1 were obtained between the agents M1 and V1 as a result of colorimetric measurements. The table shows the averages of five determination processes. The larger the value, the better the washing performance of M1 compared to V1.

TABLE 1

| Stain | agent M1 |
|---|---|
| Sebum according to Bey with carbon black | 2.1 |
| Olive oil | 1.1 |
| Pigment/oil on cotton/polyester | 1.3 |

What is claimed is:

1. A washing or cleaning agent for washing laundry or cleaning hard surfaces comprising:
   a) from 5 to 65 wt. % of an anionic surfactant of general formula (I),

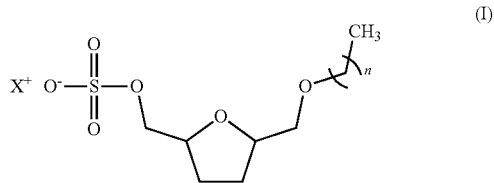

in which n represents a number from 5 to 21, and $X^+$ represents a charge-balancing cation; and,
   b) from 5 to 65 wt. % of a further surfactant.

2. The washing or cleaning agent according to claim 1, characterized in that it is particulate and contains builders.

3. The washing or cleaning agent according to claim 1, characterized in that it is liquid and contains from 1 wt. % to 90 wt. % of water, a water-miscible solvent or a mixture of water and a water-miscible solvent.

4. The washing or cleaning agent according to claim 1, characterized in that it is provided in a chamber made of water-soluble material such that it is portioned so as to be ready to be dispensed in individual portions, and contains less than 15 wt. % of water.

5. The washing or cleaning agent according to claim 1, characterized in that, in the compound of general formula (I), n represents a number from 7 to 17.

6. The washing or cleaning agent according to claim 1, characterized in that, in the compound of general formula (I), $X^+$ is selected from the group consisting of the proton, alkali metal cations and the group $N^+R^1R^2R^3$, in which $R^1$, $R^2$ and $R^3$ represent, independently of one another, hydrogen, an alkyl group having 1 to 6 C atoms or a hydroxyalkyl group having 2 to 6 C atoms.

7. The washing or cleaning agent according to claim 2, characterized in that it contains builders in an amount from 1 wt. % to 60 wt. %.

8. The washing or cleaning agent according to claim 3, characterized in that it-contains from 10 wt. % to 85 wt. % of water, a water-miscible solvent or a mixture of water and a water-miscible solvent.

9. The washing or cleaning agent according to claim 4, characterized in that it is to be dispensed in individual portions, and contains from 1 wt. % to 12 wt. % of water.

* * * * *